US012161296B2

(12) United States Patent
Govari et al.

(10) Patent No.: US 12,161,296 B2
(45) Date of Patent: Dec. 10, 2024

(54) AUGMENTED-REALITY VISUALIZATION OF AN OPHTHALMIC SURGICAL TOOL

(71) Applicant: JOHNSON & JOHNSON SURGICAL VISION, INC., Irvine, CA (US)

(72) Inventors: Assaf Govari, Haifa (IL); Vadim Gliner, Haifa (IL)

(73) Assignee: Johnson & Johnson Surgical Vision, Inc., Irvine, CA (US)

(*) Notice: Subject to any disclaimer, the term of this patent is extended or adjusted under 35 U.S.C. 154(b) by 836 days.

(21) Appl. No.: 17/221,908

(22) Filed: Apr. 5, 2021

(65) Prior Publication Data

US 2021/0330394 A1 Oct. 28, 2021

Related U.S. Application Data

(60) Provisional application No. 63/014,383, filed on Apr. 23, 2020, provisional application No. 63/014,402, (Continued)

(51) Int. Cl.
*A61B 34/20* (2016.01)
*A61B 1/00* (2006.01)
(Continued)

(52) U.S. Cl.
CPC ...... *A61B 1/00158* (2013.01); *A61B 1/00009* (2013.01); *A61B 5/062* (2013.01); (Continued)

(58) Field of Classification Search
CPC . A61B 34/20; A61B 90/36; A61B 2034/2059; A61B 2090/365; A61B 2034/2051; A61B 2034/2055; A61B 1/00158; A61B 1/00009; A61B 5/0013; A61B 2090/371; A61B 2090/372; A61B 2090/3762; A61B 2090/3979; A61B 2505/05; A61B 1/0005; A61B 3/0041; A61B 5/6847; A61B 5/743; A61B 90/20;
(Continued)

(56) References Cited

U.S. PATENT DOCUMENTS 5,391,199 A 2/1995 Ben-Haim
6,239,724 B1 5/2001 Doron et al.
(Continued)

FOREIGN PATENT DOCUMENTS

EP 0951874 A2 10/1999
EP 1829477 A2 9/2007
(Continued)

*Primary Examiner* — Jeffery A Brier (57) ABSTRACT

A system includes a processor and a display. The processor is configured to: (a) receive an optical image of an organ of a patient, (b) receive an anatomical image of the organ, (c) receive, from a position tracking system (PTS), a position signal indicative of a position of a medical instrument treating the organ, (d) register the optical image and the anatomical image in a common coordinate system, and (e) estimate the position of the medical instrument in at least one of the optical image and the anatomical image. The display is configured to visualize the medical instrument overlaid on at least one of the optical image and the anatomical image.

20 Claims, 3 Drawing Sheets

Related U.S. Application Data filed on Apr. 23, 2020, provisional application No. 63/014,376, filed on Apr. 23, 2020.

(51) Int. Cl.
*A61B 5/06* (2006.01)
*A61B 90/00* (2016.01)
*A61F 9/007* (2006.01)

(52) U.S. Cl.
CPC .............. *A61B 34/20* (2016.02); *A61B 90/36* (2016.02); *A61F 9/007* (2013.01); *A61B 2034/2051* (2016.02); *A61B 2034/2055* (2016.02); *A61B 2034/2059* (2016.02); *A61B 2090/365* (2016.02)

(58) Field of Classification Search
CPC ...... A61B 2090/3983; A61B 2090/502; A61B 5/062; A61B 5/6821; A61F 9/007; A61F 9/00736
See application file for complete search history.

(56) References Cited

U.S. PATENT DOCUMENTS

| | | |
|---|---|---|
| 6,332,089 B1 | 12/2001 | Acker et al. |
| 6,381,485 B1 | 4/2002 | Hunter et al. |
| 6,484,118 B1 | 11/2002 | Govari |
| 6,498,944 B1 | 12/2002 | Ben-Haim et al. |
| 6,618,612 B1 | 9/2003 | Acker et al. |
| 6,690,963 B2 | 2/2004 | Ben-Haim et al. |
| 8,180,430 B2 | 5/2012 | Govari et al. |
| 2002/0065455 A1 | 5/2002 | Ben-Haim et al. |
| 2003/0023161 A1 | 1/2003 | Govari et al. |
| 2003/0120150 A1 | 6/2003 | Govari |
| 2004/0068178 A1 | 4/2004 | Govari |
| 2004/0101086 A1* | 5/2004 | Sabol .................. A61B 6/4241 378/4 |
| 2004/0199072 A1 | 10/2004 | Sprouse et al. |
| 2005/0054900 A1 | 3/2005 | Mawn et al. |
| 2005/0203380 A1 | 9/2005 | Sauer et al. |
| 2006/0161062 A1* | 7/2006 | Arditi ...................... A61B 8/13 600/443 |
| 2006/0281971 A1 | 12/2006 | Sauer et al. |
| 2007/0265526 A1 | 11/2007 | Govari et al. |
| 2013/0015848 A1 | 1/2013 | Govari et al. |
| 2013/0060146 A1 | 3/2013 | Yang et al. |
| 2013/0245461 A1 | 9/2013 | Maier-Hein et al. |
| 2014/0275760 A1 | 9/2014 | Lee et al. |
| 2015/0272694 A1 | 10/2015 | Charles |
| 2015/0327948 A1 | 11/2015 | Schoepp et al. |
| 2015/0366628 A1 | 12/2015 | Ingmanson |
| 2016/0015469 A1 | 1/2016 | Goshayesh |
| 2017/0007155 A1 | 1/2017 | Gliner |
| 2017/0007156 A1 | 1/2017 | Govari et al. |
| 2017/0172696 A1 | 6/2017 | Saget et al. |
| 2017/0280989 A1 | 10/2017 | Heeren |
| 2017/0367771 A1 | 12/2017 | Tako et al. |
| 2018/0068441 A1 | 3/2018 | Yu et al. |
| 2018/0098816 A1 | 4/2018 | Govari et al. |
| 2018/0220100 A1 | 8/2018 | Ovchinnikov et al. |
| 2018/0228392 A1 | 8/2018 | Govari et al. |
| 2018/0245461 A1 | 8/2018 | Barak |
| 2018/0270436 A1 | 9/2018 | Ivarsson et al. |
| 2018/0286132 A1 | 10/2018 | Cvetko et al. |
| 2018/0325608 A1 | 11/2018 | Kang et al. |
| 2019/0058859 A1 | 2/2019 | Price et al. |
| 2019/0083115 A1 | 3/2019 | Bar-Tal |
| 2019/0159843 A1 | 5/2019 | Demri et al. |
| 2019/0192232 A1 | 6/2019 | Altmann et al. |
| 2019/0209116 A1* | 7/2019 | Sjöstrand ............... G16H 50/30 |
| 2019/0365346 A1 | 12/2019 | Elliot et al. |
| 2020/0015923 A1 | 1/2020 | Scheib |
| 2020/0188173 A1 | 6/2020 | Berlin |
| 2020/0253673 A1* | 8/2020 | Azizian .................. A61B 90/36 |
| 2021/0196105 A1 | 7/2021 | Algawi et al. |
| 2021/0196384 A1* | 7/2021 | Shelton, IV .......... A61B 34/10 |
| 2021/0196424 A1* | 7/2021 | Shelton, IV .......... A61B 34/25 |
| 2021/0330393 A1 | 10/2021 | Govari et al. |
| 2021/0330395 A1 | 10/2021 | Govari et al. |
| 2021/0330396 A1 | 10/2021 | Govari et al. |

FOREIGN PATENT DOCUMENTS

| | | |
|---|---|---|
| EP | 2829218 A1 | 1/2015 |
| EP | 3400871 A1 | 11/2018 |
| EP | 3387984 B1 | 4/2020 |
| EP | 3241051 B1 | 6/2020 |
| WO | 9605768 A1 | 2/1996 |
| WO | 2019141704 A1 | 7/2019 |
| WO | 2021076560 A1 | 4/2021 |

* cited by examiner

AUGMENTED-REALITY VISUALIZATION OF AN OPHTHALMIC SURGICAL TOOL

CROSS-REFERENCE TO RELATED APPLICATIONS

This application claims the benefit of U.S. Provisional Patent Applications 63/014,376, 63/014,383 and 63/014,402, all filed on Apr. 23, 2020, whose disclosures are incorporated herein by reference.

FIELD OF THE INVENTION

The present invention relates generally to medical devices, and particularly to methods and systems for tracking and visualizing medical instruments in ophthalmic procedures.

BACKGROUND OF THE INVENTION

During a minimally invasive medical procedure, such as an ophthalmic procedure, a surgeon navigates a medical instrument to a target location within a patient eye. In some cases, patient tissue may obstruct at least part of the medical instrument. Various techniques have been developed for tracking and visualizing medical instruments during minimally invasive procedures.

For example, U.S. Patent Publication No. 2018/0220100 describes a system including an augmented reality device communicatively coupled to an imaging system of an ophthalmic microscope. The augmented reality device may include a lens configured to project a digital image, a gaze control configured to detect a focus of an eye of an operator, and a dimming system communicatively coupled to the gaze control and the outer surface. The system including a processor that receives a digital image from the imaging system, projects the digital image on the lens, receives a signal from the gaze control regarding the focus of the eye of the operator, and transitions the outer surface of the augmented reality device between at least partially transparent to opaque based on the received signal.

U.S. Patent Publication No. 2018/0245461 describes a sensor, employed to sense a distance to the surface of a subject to be examined, so that a range image may be acquired. Intensity information may be acquired alongside the distance information. The distance information and intensity information may be evaluated to track the pose of the sensor means relative to the surface of the subject to be examined, so that anatomical data related to said subject may be displayed as seen from the position and/or orientation of the sensor means or display means.

U.S. Patent Publication No. 2004/0199072 describes a patient positioning device used for positioning a patient during a navigated medical procedure. The positioning device includes a contoured patient support and a portion of a navigation system. The contoured patient support positions the patient in a desired manner. The portion of the navigation system is integrated within the patient support, such that the navigated medical procedure may be performed in a substantially unobstructed manner.

U.S. Patent Publication No. 2006/0281971 describes a method and apparatus for presenting three-dimensional data to a surgeon, which is provided to facilitate the flexible navigation of an endoscope and surgical instruments with respect to anatomical structures. In accordance with a first embodiment a first set of data corresponding to a three-dimensional model of a patient's anatomy is received. This three-dimensional model may be rendered from images taken in CT or MRI scanning. In accordance with this embodiment, this model is then combined with a second set of data corresponding to a view obtained from an endoscope.

SUMMARY OF THE INVENTION

An embodiment of the present invention that is described herein provides a system including a processor and a display. The processor is configured to: (a) receive an optical image of an organ of a patient, (b) receive an anatomical image of the organ, (c) receive, from a position tracking system (PTS), a position signal indicative of a position of a medical instrument treating the organ, (d) register the optical image and the anatomical image in a common coordinate system, and (e) estimate the position of the medical instrument in at least one of the optical image and the anatomical image. The display is configured to visualize the medical instrument overlaid on at least one of the optical image and the anatomical image.

In some embodiments, at least part of the medical instrument is obstructed by a blocking element, and the processor is configured to display the position of the medical instrument unobstructed. In other embodiments, when at least part of the medical instrument is obstructed, the processor is configured to display the medical instrument overlaid on the anatomical image. In yet other embodiments, the processor is configured to display the blocking element transparent so as to display the position of the medical instrument unobstructed.

In an embodiment, the blocking element includes tissue. In another embodiment, the display is configured to visualize the medical instrument overlaid on at least one of the optical image and the anatomical image, based on the position signal, which is received from the PTS and is indicative of the position of the medical instrument. In yet another embodiment, the optical image includes a stereoscopic image.

In some embodiments, the display includes an augmented reality display, and the processor is configured to simultaneously display, on the display, the optical image on a first section of the display, and the anatomical image on a second section of the display. In other embodiments, the common coordinate system includes a coordinate system of the PTS. In yet other embodiments, the organ includes an eye of the patient.

There is additionally provided, in accordance with an embodiment of the present invention, a method including receiving an optical image of an organ of a patient and an anatomical image of the organ. A position signal indicative of a position of a medical instrument treating the organ is received from a position tracking system (PTS). The optical image and the anatomical image are registered in a common coordinate system. The position of the medical instrument is estimated in at least one of the optical image and the anatomical image. The medical instrument, overlaid on at least one of the optical image and the anatomical image, is visualized.

There is further provided, in accordance with an embodiment of the present invention: a medical instrument, a position sensor of a position tracking system (PTS), a processor and a display. The medical instrument is configured to treat an organ of a patient. The position sensor is coupled to the medical instrument, and is configured to produce a position signal indicative of a position of the medical instrument. The processor is configured to: (a) receive (i) an optical image and an anatomical image of the organ, and (ii) the position signal, (b) register the optical image and the anatomical image in a common coordinate system, and (c) estimate the position of the medical instrument in at least one of the optical image and the anatomical image. The display is configured to visualize the medical instrument overlaid on at least one of the optical image and the anatomical image.

In some embodiments, the display includes an augmented reality display, and the processor is configured to simultaneously display, on the display, the optical image on a first section of the display, and the anatomical image on a second section of the display. In other embodiments, the organ includes an eye of the patient, and the medical instrument includes an ophthalmic surgical tool, which is configured to conduct an ophthalmic surgical procedure in the patient eye.

The present invention will be more fully understood from the following detailed description of the embodiments thereof, taken together with the drawings in which:

DETAILED DESCRIPTION OF EMBODIMENTS

Overview

Accurate position tracking and visualization of a medical instrument are particularly important in surgical procedures carried out in small organs, such as in a patient eye.

Embodiments of the present invention that are described hereinbelow provide improved techniques for tracking and visualizing a medical instrument, which is at least partially obstructed or hidden from view to a surgeon during an ophthalmic surgical procedure.

In some embodiments, an ophthalmic surgical system comprises a location pad having a frame made from a flexible substrate, such as a flexible printed circuit board (PCB), which is configured to be attached to facial tissue surrounding at least part of a patient eye. In some embodiments, the location pad comprises multiple field-generators of a position tracking system (PTS), which are coupled to the frame at respective positions surrounding at least a portion of the eye and are configured to generate respective magnetic fields at least in a region-of-interest (ROI) of the patient eye.

In some embodiments, the ophthalmic surgical system comprises a surgical tool having one or more position sensors of the PTS, which is coupled to the surgical tool, for example in an embodiment, the sensor is coupled with the distal end of the surgical tool, and is configured to sense the magnetic fields. In response to sensing the magnetic fields, the position sensor is configured to produce a position signal indicative of the position of the surgical tool, such as the distal end, in the ROI.

In some embodiments, the ophthalmic surgical system comprises a processor, which is configured to receive one or more of (a) a stereoscopic optical image of the patient eye, (b) an anatomical image, such as a computerized tomography image (CTI), of the patient eye, and (c) a position signal of the PTS. The processor is further configured to register the optical image and the anatomical image in a coordinate system of the PTS, and to estimate the position of the medical instrument in at least one of the optical image and the CTI.

In some embodiments, the ophthalmic surgical system comprises a display, which is configured to visualize the medical instrument overlaid on at least one of the optical image and the CTI. In some cases, eye tissue or any other blocking element, may obstruct or conceal (from the surgeon's view) at a portion of the surgical tool, like the distal end of the surgical tool, at for example, the ROI. In some embodiments, the display comprises an augmented reality display, and the processor is configured to display, on the display, the position of the medical instrument unobstructed. For example, the processor is configured to simultaneously display the optical image surrounding the ROI, and the CTI on the ROI, so as to visualize the estimated position of the surgical tool in the ROI.

In some embodiments, the location pad comprises tracking elements, fixed at predefined positions on the frame for registering the location pad with the patient eye. The tracking elements may comprise infrared light emitting diodes (LEDs), each of which having a different flashing rate. In some embodiments, the augmented reality display comprises a head mount display (HMD) having an image sensor, which is configured to acquire infrared images of the tracking elements during the procedure. Based on the infrared images, the processor is configured to improve the registration between the ROI and the coordinate system of the PTS, so as to improve the accuracy and visualization of the estimated position of the surgical tool during the ophthalmic procedure.

The disclosed techniques improve the quality of a medical procedure carried out in an organ, by visualizing a hidden section of a medical instrument operated within a ROI of the organ. Specifically, the disclosed techniques improve the positioning accuracy of a surgical tool in a small organ.

System Description

Figure 1:
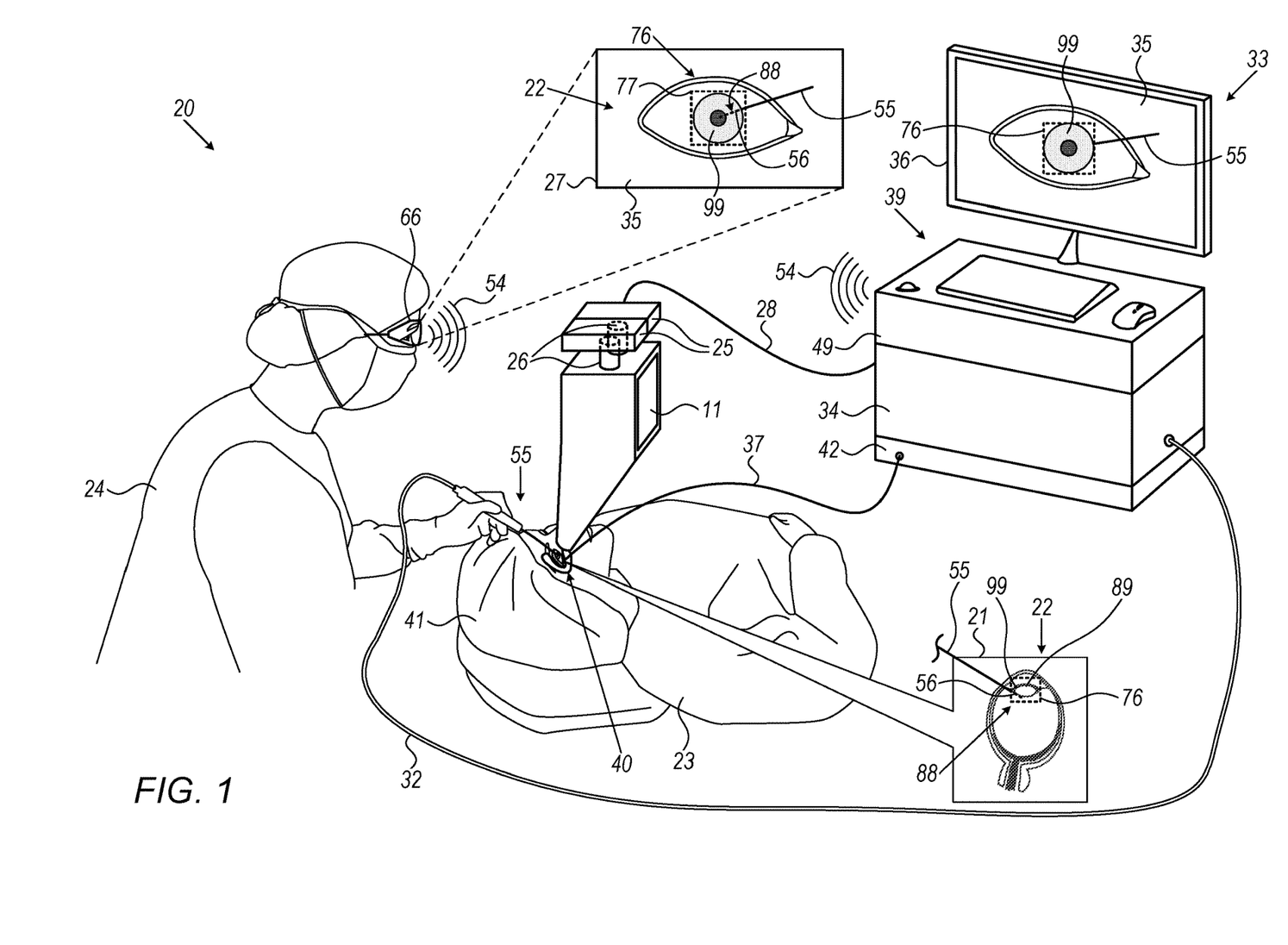
FIG. 1 is a schematic pictorial illustration of an ophthalmic surgical system, in accordance with an embodiment of the present invention.

FIG. 1 is a schematic pictorial illustration of an ophthalmic surgical system 20, in accordance with an embodiment of the present invention. System 20 is configured to carry out various types of ophthalmic procedures, such as but not limited to a cataract surgery.

In some embodiments, system 20 comprises a medical instrument, such as but not limited to a phacoemulsification handpiece or any other suitable type of an ophthalmic surgical tool, referred to herein as a tool 55, used by a surgeon 24 to carry out the ophthalmic surgical procedure. Other surgical tools may comprise an irrigation and aspiration (I/A) handpiece, a diathermy handpiece, a vitrectomy handpiece, and similar instruments.

Reference is now made to an inset 21 showing a sectional view of the surgical procedure carried out in an eye 22 of a patient 23. In some embodiments, surgeon 24 applies tool 55 for treating eye 22, in the present example, surgeon 24 inserts a distal end 88 of tool 55 into a region-of-interest (ROI) 76 of eye 22. In the example of inset 21, during a cataract surgical procedure, surgeon 24 inserts tool 55 below iris tissue 99 so as to apply phacoemulsification to a lens 89 of eye 22.

In some embodiments, tool 55 comprises one or more position sensor(s) 56 of a magnetic position tracking system (PTS) described in detail below. At least one position sensor 56 may comprise a triple-axis sensor (TAS) made from three coils or a single-axis sensor (SAS) implemented on a printed circuit board (PCB) or using any other suitable technique. Magnetic position sensors are described in further detail, for example in U.S. Pat. Nos. 6,498,944 and 6,690,963, and in U.S. patent Publication No. 2018/0228392, whose disclosures are all incorporated herein by reference. The one or more position sensor(s) 56 may be located anywhere on tool 55, for example, anywhere on a shaft of the tool or a portion of the tool located near the treatment site. In the present example, position sensor 56 is coupled to distal end 88 of tool 55.

Additionally or alternatively, the PTS may comprise any other suitable type of PTS, such as but not limited to an optical-based PTS or an impedance-based PTS. In such embodiments, at least one position sensor 56 may have a suitable structure other than the one or more coils described above.

Reference is now made back to the general view of FIG. 1. In some embodiments, system 20 comprises a location pad 40 having a frame and a plurality of field-generators shown and described in detail in FIG. 2 below. In some embodiments, location pad 40 comprises a flexible substrate, which is configured to be attached to facial tissue (e.g., skin) of patient 23. In the context of the present disclosure, and in the claims, using the term "attached" means that, when head 41 of patient 23 is moved in a given offset, location pad 40 is moved in the same offset. In other words, location pad 40 and head 41 are considered to be a single rigid body.

In an embodiment, system 20 comprises the aforementioned magnetic position tracking system, which is configured to track the position of one or more position sensors, such as position sensor 56 located on tool 55 that is used for treating eye 22, and/or other position sensors coupled to tools inserted into head 41, eye 22, or into any other organ of patient 23. In an embodiment, the magnetic position tracking system comprises magnetic field-generators (not shown) fixed at respective positions of the aforementioned frame of location pad 40, whose details are shown and described in FIG. 2 below.

In some embodiments, position sensor 56 is configured to generate one or more position signals in response to sensing external magnetic fields generated by the field-generators of location pad 40. In some embodiments, a processor 34 (described in detail below) of system 20 is configured to estimate, based on the position signals, the position of tool 55, e.g. distal end 88, within ROI 76 of eye 22.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Publication Nos. 2002/0065455 A1, 2003/0120150 A1 and 2004/0068178 A1, whose disclosures are all incorporated herein by reference.

In some embodiments, system 20 comprises a console 33, which comprises a memory 49, and a driver circuit 42 configured to drive, via a cable 37, the field-generators with suitable signals so as to generate magnetic fields in a predefined working volume, such as in ROI 76 of eye 22.

In some embodiments, console 33 comprises processor 34, typically a general-purpose computer, with suitable front end and interface circuits for receiving the position signals from position sensor 56 coupled to tool 55. In the present example, processor 34 receives the position signals via a cable 32; and may use cable 32 for exchanging any suitable signals with other components of tool 55. Other means of transmitting and receiving signals known in the art are also contemplated, e.g. BLUETOOTH or other wireless connection. Console 33 further comprises input device 39 and a display 36 (which may also be, for example, a keyboard, touch screen graphical user interface, or the like).

In some embodiments, system 20 comprises an ophthalmic surgical microscope 11, such as ZEISS OPMI LUMERA series or ZEISS ARTEVO series supplied by Carl Zeiss Meditec AG (Oberkochen, Germany), or any other suitable type of ophthalmic surgical microscope provided by other suppliers. Ophthalmic surgical microscope 11 is configured to produce stereoscopic optical images and two-dimensional (2D) optical images of eye 22. In some embodiments, system 20 comprises two cameras 25 coupled, respectively, to two eyepieces 26 of ophthalmic surgical microscope 11, and configured to acquire two respective optical images of eye 22.

In some embodiments, the coupling between cameras 25 and eyepieces 26 may be carried out using a suitable jig, or any other suitable method and/or apparatus.

In some embodiments, processor 34 is configured to receive the optical images from cameras 25, via a cable 28 (although other means of transmitting and receiving signals known in the art may be used), and, based on the received optical images, to display an optical image 35 on display 36. Note that processor 34 is configured to display in image 35: (i) a stereoscopic image by using two separate optical paths with two objectives and eyepieces 26 to provide slightly different viewing angles to two respective cameras 25, or (ii) a 2D optical image, e.g., by using an optical image received from one selected camera 25 of system 20. Note that in most cases surgeon 24 may prefer using the stereoscopic image in such surgical applications.

As shown in the sectional view of inset 21, surgeon 24 inserts distal end 88 of tool 55 below iris tissue 99. Therefore, iris tissue 99 constitutes a blocking element for imaging distal end 88 in optical image 35. In other words, by looking at optical image 35 on display 36, surgeon 24 cannot see the location of distal end 88 due to the blocking element within ROI 76, so as to accurately emulsify lens 89 of eye 22.

In some embodiments, processor 34 is configured to receive, from an anatomical imaging system, such as a computerized tomography (CT) system (not shown), a three-dimensional (3D) anatomical image acquired prior to the ophthalmic procedure.

In some embodiments, system 20 comprises an optical head mount display (HMD) 66 using augmented reality techniques for visualizing distal end 88 of tool 55 overlaid on at least one of optical image 35 and the anatomical image, as described herein.

Reference is now made to an inset 27 showing a displayed augmented image described herein. In an embodiment, processor 34 is configured to select, from the 3D anatomical image, a 2D slice of the anatomical image comprising CT imaging of ROI 76, referred to herein as a CT image (CTI) 77.

As described above, distal end 88 of tool 55 may be invisible in optical image 35, for being obstructed by a blocking element (e.g., iris tissue 99, any other tissue, or a medical apparatus used in the ophthalmic procedure). In some embodiments, based on optical image 35, CTI 77, and the position signal received from position sensor 56, processor 34 is configured to display the position of distal end 88 unobstructed. In the example of inset 27, the visualization of distal end 88 is shown as a dashed line.

In some embodiments, HMD 66 and console 33 have wireless devices (not shown) configured to exchange wireless signals 54 for transferring, inter alia, the aforementioned augmented image and/or any suitable combination of image 35, CTI 77, and the position signals of position sensor 56.

In an embodiment, processor 34 is configured to display, on HMD 66, a visualization of distal end 88 overlaid on CTI 77. In the example of inset 27, processor 34 is configured to replace, in ROI 76, the section of the optical image with a corresponding CTI 77, or with any other suitable section of a slice of the CT image.

In some embodiments, using the augmented reality techniques, processor 34 is configured to display iris tissue 99 (or any other blocking element) transparent, so as to display the position of distal end 88 unobstructed.

In some embodiments, processor 34 is configured to register optical image 35 and the anatomical image (e.g., a slice comprising CTI 77) in a common coordinate system, such as a coordinate system of the position tracking system. In other words, processor 34 receives two or more of the following inputs: (a) the optical (2D or stereoscopic) image from ophthalmic surgical microscope 11, (b) the anatomical image from the CT system, and (c) the position signal (generated by position sensor 56) from the position tracking system. Subsequently, processor 34 processes at least some of the received three inputs (for example, by producing optical image 35, and/or CTI 77, and registers the coordinate systems of optical image 35, CTI 77 and the position signals received from position sensor 56, in a common coordinate system (e.g., the coordinate system of the position tracking system).

In some embodiments, after performing the registration process described above, processor 34 is configured to track the position of distal end 88, based on position signals received from one or more position sensor(s) 56. Moreover, processor 34 is configured to visualize the position of distal end 88 overlaid on at least one of the registered CTI 77 and optical image 35. In the example of inset 27, processor 34 is configured to produce the aforementioned augmented image comprising: (a) CTI 77 displayed on the section of ROI 76, (b) optical image 35 displaying tool 55 and eye 22 surrounding the section of ROI 76, and (c) a visualization of distal end 88, overlaid on CTI 77 in the section of ROI 76. In the context of the present disclosure and in the claims, the terms "produce" and "generate" are used interchangeably, e.g., for signals and images made by one or more position sensor(s) 56, processor 34 and any other component of system 20.

In some embodiments, processor 34 is configured to transmit the augmented image shown in inset 27 and described above, to HMD 66 so that surgeon 24 can see eye 22 and a visualization of the estimated position of distal end 88 of tool 55.

In some embodiments, the augmented image shown in inset 27, provides surgeon 24 with a complete visualization of tool 55, including distal end 88. In other embodiments, in order to optimize the visualization of distal end 88 during the ophthalmic procedure, processor 34 is configured to dynamically control the size of ROI 76, automatically (e.g., based on the position and/or obstruction of distal end 88) or in response to an instruction received from surgeon 24 using input device 39.

In alternative embodiments, HMD 66 may comprise a processor (not shown), which is configured to carry out at least some of the operations carried out by processor 34 and described above. In such embodiments, at least some of the signals described above (e.g., optical images from ophthalmic surgical microscope 11, CTI 77 from processor 34 or the CTI from the CT system, the position signals from position sensor(s) 56) may be transmitted directly (wirelessly or via cables) to the processor of HMD 66, which may generate and display the augmented image on HMD 66. In yet other embodiments, the operations described above may be divided, using any suitable definition, between processor 34 and the processor of HMD 66, so that the augmented image is displayed on HMD 66 as described in detail above.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of ophthalmic and other minimally invasive and surgical systems.

Figure 2:
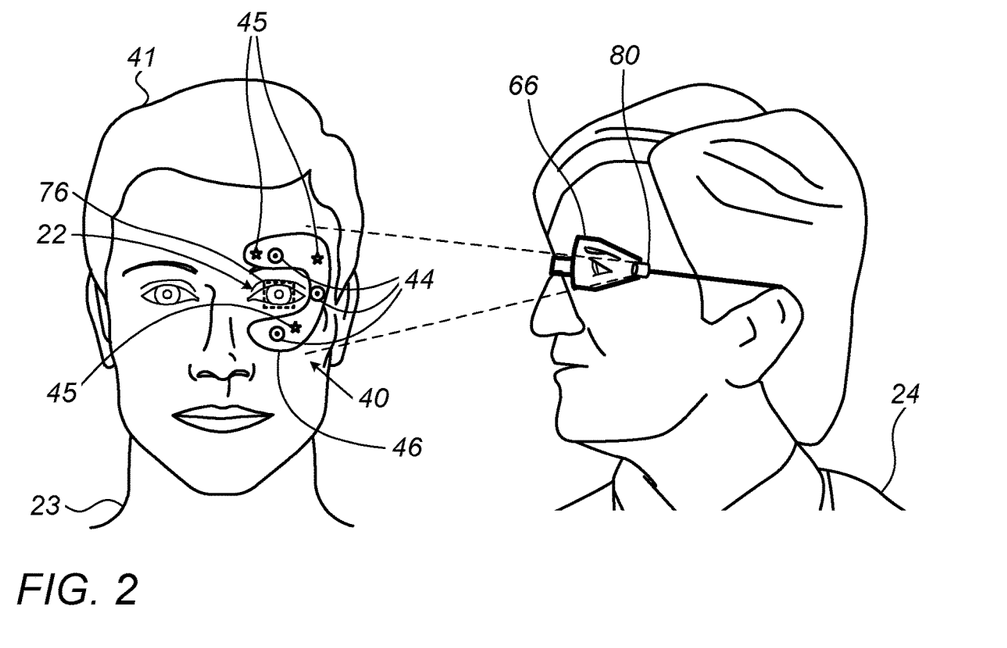
FIG. 2 is a schematic pictorial illustration of a location pad used for tracking a medical instrument treating a patient eye, in accordance with an embodiment of the present invention.

Improving Position Tracking Accuracy Using a Location Pad Surrounding Treated Eye FIG. 2 is a schematic pictorial illustration of location pad 40 used for tracking tool 55 when treating eye 22, in accordance with an embodiment of the present invention. In some embodiments, location pad 40 comprises a frame 46 made from a flexible substrate, such as a flexible printed circuit board (PCB), and a plurality of field-generators 44 coupled with frame 46.

In some embodiments, frame 46 is attached to tissue (e.g., cheek and forehead) that is at least partially surrounding eye 22 and is configured to place a plurality of field-generators 44 at respective positions surrounding ROI 76. In some embodiments, each field-generator 44 comprises one or more coils arranged in any suitable configuration, e.g., concentric or non-concentric arrangement. Several configurations of field-generators are implemented in various types of location pads, and are described in detail, for example, in U.S. Patent Publication Nos. 2007/0265526, US2017/0007156, and in U.S. Pat. No. 8,180,430, whose disclosures are all incorporated herein by reference.

In the exemplary configuration shown in FIG. 1, pad 40 comprises three field-generators 44, but may alternatively comprise any other suitable number of field-generators 44.

As described in FIG. 1 above, the magnetic position tracking system comprises magnetic field-generators 44 fixed at respective positions of frame 46 of location pad 40. Position sensor 56 is configured to generate one or more position signals in response to sensing external magnetic fields generated by the field-generators 44 of location pad 40, and processor 34 is configured to estimate, based on the one or more position signals, the position of distal end 88 within ROI 76 of eye 22.

In principle, it is possible to use any suitable type of location pad having field-generators generating respective magnetic fields at least in ROI 76. For example, U.S. Patent Publication No. 2018/0098816, whose disclosure is incorporated herein by reference, describes a location pad surrounding head 41 used for ear-nose-throat (ENT) applications. Such location pads, however, do not enable positioning accuracy sufficient for performing a cataract surgical procedure, mainly because of insufficient proximity between the field-generators and the ROI in which the surgeon performs the procedure. For example, a cataract surgery procedure requires a sub-millimeter positioning accuracy, which can be obtained when field-generators 44 are positioned in close proximity to ROI 76. Moreover, any movement of head 41 may spoil the registration between optical image 35, CTI 77 and position signals produced by position sensor 56, and therefore may degrade the quality of the cataract surgical procedure.

In some embodiments shown in FIG. 2, location pad 40 is attached to and conforms to the skin surrounding at least part of eye 22. Therefore, location pad 40 moves together with head 41, so that any movement of head 41 may not spoil the registration described in FIG. 1 above.

In some embodiments, the close proximity between ROI 76 and the surrounding field-generators 44 improves the positioning accuracy of the position sensor(s) 56 in the coordinate system of the position tracking system. The improved positioning accuracy results in improved overlay accuracy of distal end 88 visualized on the augmented image described in FIG. 1 above, and/or the overlay accuracy in at least one of optical image 35 and CTI 77.

In some embodiments, location pad 40 comprises one or more tracking elements 45 for registering location pad 40 with eye 22. In the example of FIG. 2, tracking elements 45 comprise optical tracking elements, such as infrared light emitting diodes (LEDs), each of which having a different flashing rate.

In some embodiments, HMD 66 comprises an image sensor 80, which is configured, to acquire images of the LEDs of tracking elements 45, and to send the images (e.g., carried on wireless signals 54 as described in FIG. 1 above) to processor 34, e.g., during the cataract surgical procedure.

In some embodiments, based on the received images of the LEDs of tracking elements 45, processor 34 is configured to dynamically update (e.g., in real-time) the registration between ROI 76 and the coordinate system of the PTS (or any other common coordinate system). The real-time registration may improve the quality of the cataract surgical procedure, by improving the accuracy and visualization of the estimated position of distal end 88 in ROI 76.

In other embodiments, location pad 40 may comprise any other suitable type of LEDs or other sorts of tracking elements. Moreover, in the example of FIG. 2, location pad comprises three tracking elements 45, but in other embodiments, location pad 40 may have any other suitable number tracking elements 45, typically but not necessarily, arranged around eye 22.

This particular configuration of location pad 40 is shown by way of example, in order to illustrate certain alignment and/or registration problems that are addressed by embodiments of the present invention and to demonstrate the application of these embodiments in enhancing the performance of system 20. Embodiments of the present invention, however, are by no means limited to this specific sort of example location pad and/or system, and the principles described herein may similarly be applied to other sorts of location pads and/or medical systems. For example, in FIG. 2 frame 46 has a horseshoe shape partially surrounding eye 22 and open at the side of the patient nose, in other embodiments, frame 46 may have any other suitable shape, e.g., a bagel-shape fully surrounding eye 22, or a goggles-shape or eye-mask shape comprising two bagel-shaped frames fully surrounding both eyes of patient 23.

Moreover, in some embodiments, a substantially identical location pad 40 may be flipped 180° for being used on the second eye of patient 23. In other embodiments, a location pad for the second eye may have a horseshoe shape open at the side of the patient nose, e.g., having a symmetric configuration to that of location pad 40.

In other embodiments, the location pad frame may have any other suitable shape and may have any suitable number of at least field-generators 44 at suitable respective positions. In such embodiments, the location pad may have only field-generators 44 fixed on the frame. In alternative embodiments, the location pad may have both field-generators 44 and tracking elements fixed on the frame having any suitable shape.

Figure 3:
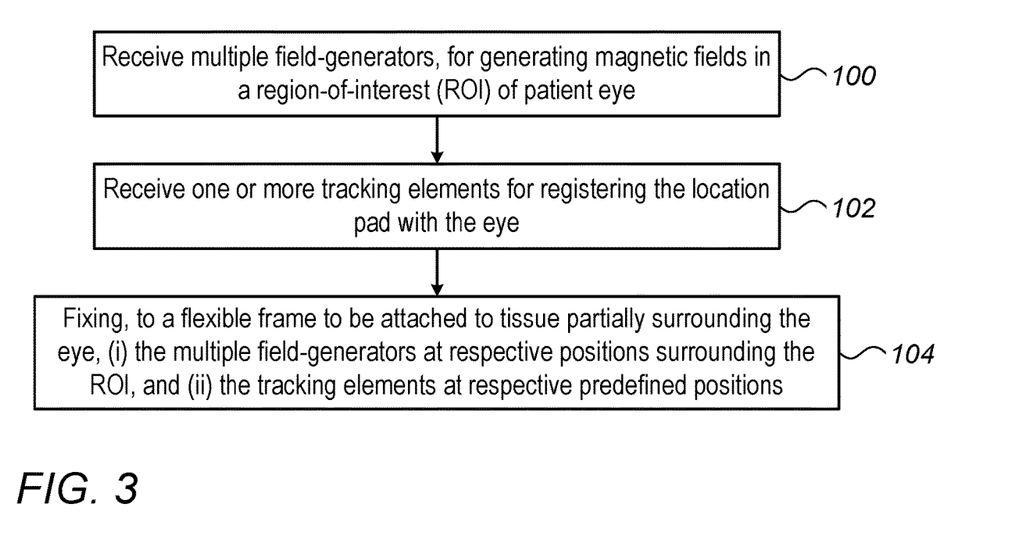
FIG. 3 is a flow chart that schematically illustrates a method for producing a location pad, in accordance with an embodiment of the present invention.

Producing Location Pad Adapted to be Attached to Tissue Surrounding Patient Eye FIG. 3 is a flow chart that schematically illustrates a method for producing location pad 40, in accordance with an embodiment of the present invention. The method begins at a step 100 with receiving one or more field-generators 44 for generating magnetic fields at least in a ROI of eye 22.

At a step 102, receiving tracking elements 45, such as infrared LEDs or any other suitable tracking elements, for registering location pad 40 with eye 22. At a step 104, field-generators 44 and tracking elements 45 are fixed to frame 46.

In some embodiments, frame 46 comprises a flexible substrate, such as the aforementioned flexible PCB, which is configured to (a) conform to the shape and geometry of facial tissue surrounding at least part of eye 22, and (b) be attached to the facial tissue, so that head 41 and frame 46 of location pad 40 are moving together as a single unit. In such embodiments, when head 41 is moved by a given offset during the ophthalmic procedure, frame 46 is moved in the same offset, so that location pad 40 remains at the same position relative to eye 22 and/or head 41 and particularly to ROI 76, as described in FIG. 2 above.

In some embodiments, in step 102 both field-generators 44 and tracking elements 45 are fixed to frame 46 at respective positions surrounding at least a portion of ROI 76, and in alternative embodiments, field-generators 44 and tracking elements 45 surrounding ROI 76. Field-generators 44 are arranged at first respective positions for obtaining the specified magnetic fields, at least within ROI 76. Tracking elements 45 are arranged at second respective positions for obtaining the specified physical registration between location pad 40 and ROI 76 within eye 22.

In the example of FIG. 2, the first and second positions differ from one another, but in other embodiments, at least one field-generator 44 and one tracking element 45 may be fixed at the same position on frame 46.

In alternative embodiments, tracking element 45 may not be fixed on frame 46 and only field-generators 44 may be attached to frame 46 for producing the respective magnetic fields. This configuration may be used, for example, when not using augmented reality techniques, or when accurate registration between the eye and location pad is not required.

Figure 4:
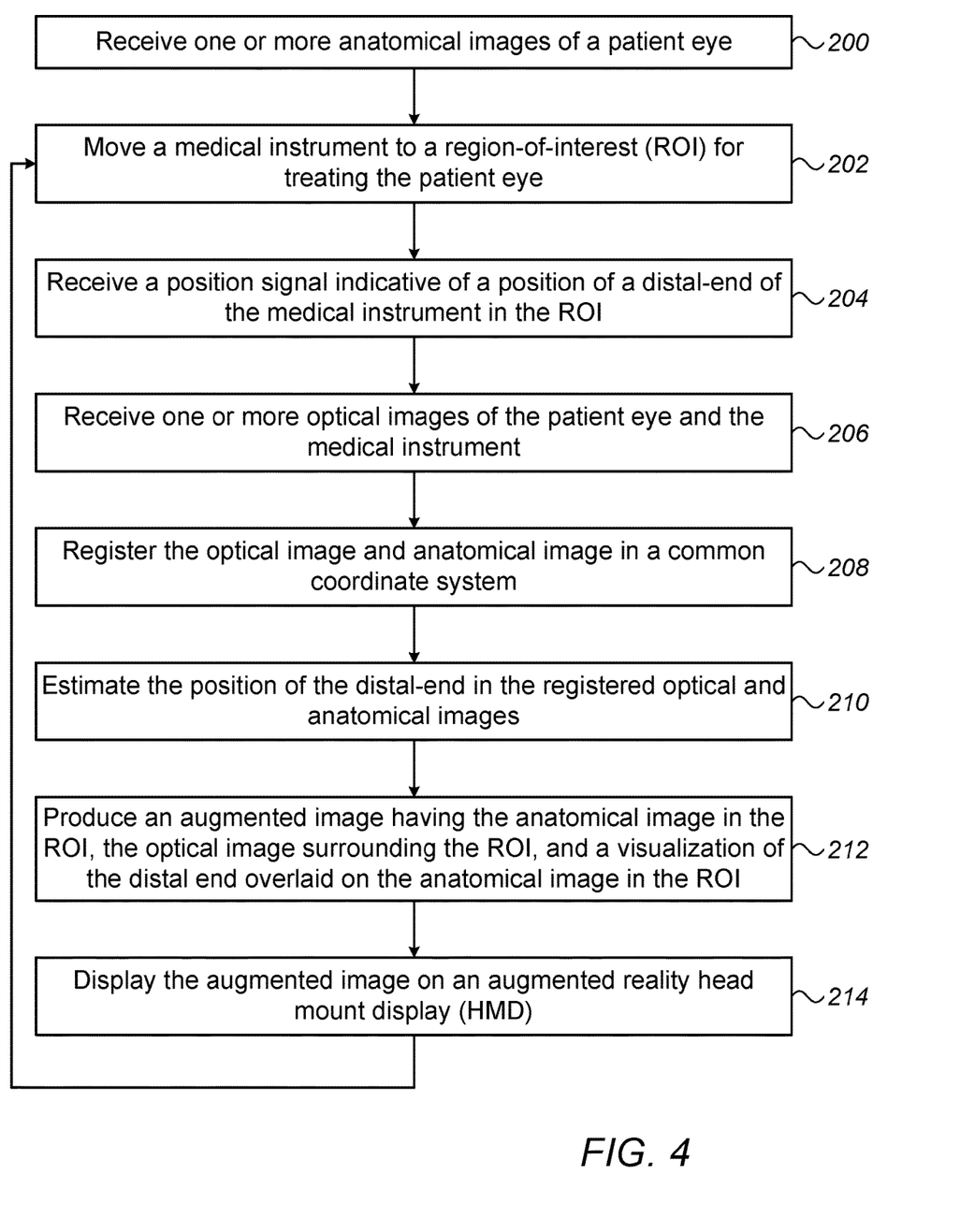
FIG. 4 is a flow chart that schematically illustrates a method for augmented-reality visualization of an ophthalmic surgical tool, in accordance with an embodiment of the present invention.

Visualizing Ophthalmic Surgical Tool Overlaid on Registered Anatomical and Optical Images FIG. 4 is a flow chart that schematically illustrates a method for augmented-reality visualization of tool 55 overlaid on registered CTI 77 and optical image 35, in accordance with an embodiment of the present invention. In the description below, the method is implemented on processor 34, but in other embodiments, the method may be implemented, mutatis mutandis, on any other suitable type of computing device or system.

The method begins at an anatomical image receiving step 200, with processor 34 receiving one or more anatomical images (e.g., CT images) of patient eye 22. As described in FIG. 1 above, processor 34 produces CTI 77, which is a 2D slice of the anatomical image comprising the CT imaging of ROI 76.

At a medical instrument moving step 202, after inserting tool 55 into or onto patient eye 22, surgeon 24 moves tool 55 to ROI 76 for treating patient eye 22, e.g., for removing the cataract using phacoemulsification. At a position signal receiving step 204, processor 34 receives, e.g., from position sensor 56, a position signal indicative of the position of distal end 88 of tool 55 within ROI 76, as described in FIG. 1 above. At an optical image receiving step 206, processor 34 receives, e.g., from ophthalmic surgical microscope 11, one or more stereoscopic or 2D optical images of eye 22 and tool 55. In some embodiments, based on the received images, processor 34 produces optical image 35 of eye 22, as described in FIG. 1 above.

At a registration step 208, processor 34 registers optical image 35 and CTI 77 (or any other suitable type of anatomical image), in a common coordinate system. For example, in the coordinate system of the position tracking system, as described in FIG. 1 above. At a position estimation step 210, processor 34 estimates, based on the one or more position signals received from position sensor 55, the position of distal end 88 in the registered optical image 35 and CTI 77, as described in FIG. 1 above.

At an augmented imaging step 212, processor 34 produces the augmented image shown in inset 27 and described in detail in FIG. 1 above. In some embodiments, the augmented image comprises CTI 77 in ROI 76, optical image 35 surrounding ROI 76, and a visualization of distal end 88 overlaid on CTI 77 shown in ROI 76.

At a displaying step 214, processor 34 displays the augmented image (e.g., the image shown in inset 27) on HMD 66 or on any other suitable type of augmented reality display. Note that optical image 35 also displays tool 55 shown out of ROI 76, therefore, surgeon 24 can see both tool 55 and distal end 88 in the augmented image shown, for example, in inset 27 of FIG. 1 above.

In some embodiments, surgeon 24 may decide to carry out the procedure at more than one location within eye 22. In such embodiments, after displaying step 214, the method may loop back to moving step 202, in which surgeon 24 moves distal end 88 to a different location within eye 22. In these embodiments, the position of the ROI within eye 22, could be updated relative to the original position of ROI 76, in response to the updated position, surgeon 24 moves tool 55 as described in step 202 above, and the method is carried out using the same steps, mutatis mutandis, of FIG. 4.

In some embodiments, in the phacoemulsification procedure after breaking up and evacuating a cloudy lens 89 from eye 22, surgeon 24 may use ophthalmic surgical microscope 11, or any other suitable image acquisition sensor, for inspecting eye 22 and verifying that eye 22 does not have residues of lens 89. After the verification, surgeon 24 may extract tool 55 out of patient eye 22 and start implanting, in eye 22, an intraocular lens (IOL) (not shown) in place of the aspirated lens 89.

Although the embodiments described herein mainly address ophthalmic procedures, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a processor, which is configured to:
receive an optical image of an organ of a patient;
receive an anatomical image of the organ;
receive, from a position tracking system (PTS), a position signal indicative of a position of at least one portion of a medical instrument treating the organ;
register the optical image and the anatomical image in a common coordinate system;
determine a region of interest of the organ of the patient;
identify a portion of the anatomical image corresponding to the region of interest of the organ; and
determine the position of the at least one portion of the medical instrument based on the position signal; and
a display, which is configured to display a representation of the at least one portion of the medical instrument overlaid on the portion of the anatomical image.

2. The system according to claim 1, wherein at least part of the medical instrument is obstructed from view in the optical image, and wherein the display is further configured to display a representation of the obstructed part of the medical instrument.

3. The system according to claim 2, wherein the part of the medical instrument is obstructed from view by a blocking element, and wherein the processor is further configured to cause a representation of the obstructed part of the medical instrument to be overlaid on the portion of the anatomical image.

4. The system according to claim 3, wherein the display is further configured to display the blocking element in a transparent manner to enable the obstructed part of the medical instrument to be viewed by a user or surgeon unobstructed.

5. The system according to claim 3, wherein the blocking element comprises tissue of the patient.

6. The system according to claim 1, wherein the region of interest is determined by the processor based on the position signal or user input, and wherein the processor is further configured to:
determine a portion of the optical image corresponding to the region of interest; and
cause the portion of the anatomical image to be displayed over the portion of the optical image.

7. The system according to claim 1, wherein the optical image comprises a stereoscopic image, wherein the anatomical image comprises a three-dimensional anatomical image, and wherein the portion of the anatomical image comprises a two-dimensional anatomical image.

8. The system according to claim 1, wherein the display comprises an augmented reality display, wherein the processor is further configured to cause the optical image to be displayed on a first section of the display and the anatomical image to be displayed on a second section of the display, and wherein the at least a portion of the second section overlaps with the first section.

9. The system according to claim 1, wherein the common coordinate system comprises a coordinate system of the PTS.

10. The system according to claim 1, wherein the organ comprises an eye of the patient, and wherein the region of interest comprises a portion of the eye.

11. A method, comprising:
receiving an optical image of an organ of a patient;
receiving an anatomical image of the organ;
receiving, from a position tracking system (PTS), a position signal indicative of a position of at least one portion of a medical instrument treating the organ;
registering the optical image and the anatomical image in a common coordinate system;
determining a region of interest of the organ of the patient;
identifying a portion of the anatomical image corresponding to the region of interest of the organ;
determining the position of the at least one portion of the medical instrument based on the position signal; and
displaying a representation of the at least one portion of the medical instrument overlaid on the portion of the anatomical image.

12. The method according to claim 11, wherein the organ comprises an eye of the patient, and wherein the region of interest comprises a portion of the eye.

13. The method according to claim 11, further comprising:
determine a portion of the optical image corresponding to the region of interest; and
cause the portion of the anatomical image to be displayed over the portion of the optical image.

14. A system, comprising:
a medical instrument, which is configured to treat an organ of a patient;
a position sensor of a position tracking system (PTS), which is coupled to the medical instrument, and is configured to produce a position signal indicative of a position of at least one portion of the medical instrument;
a processor, which is configured to:
receive an optical image and an anatomical image of the organ;
register the optical image and the anatomical image in a common coordinate system; and
receive the position signal from the PTS;
determine a region of interest of the organ of the patient;
identify a portion of the anatomical image corresponding to the region of interest of the organ;
determine the position of the at least one portion of the medical instrument based on the position signal; and
a display, which is configured to display the at least one portion of the medical instrument overlaid on the portion of the anatomical image.

15. The system according to claim 14, wherein the display comprises an augmented reality display, wherein the processor is configured to cause the optical image to be displayed on a first section of the display and the portion of the anatomical image to be displayed on a second section of the display, and wherein at least a portion of the second section overlaps with the first section.

16. The system according to claim 14, wherein the organ comprises an eye of the patient, and wherein the medical instrument comprises an ophthalmic surgical tool, which is configured to conduct an ophthalmic surgical procedure on the eye of the patient.

17. The system according to claim 14, wherein at least part of the medical instrument is obstructed from view in the optical image, and wherein the display is further configured to display a representation of the obstructed part of the medical instrument.

18. The system according to claim 17, wherein the part of the medical instrument is obstructed from view by a blocking element, and wherein the processor is further configured to cause the representation of the obstructed part of the medical instrument to be overlaid on the portion of the anatomical image.

19. The system according to claim 18, wherein the display is further configured to display the blocking element in a transparent manner to enable the obstructed part the medical instrument to be viewed by a user or surgeon.

20. The system according to claim 14, wherein the region of interest is determined by the processor based on the position signal or user input, and wherein the processor is further configured to:
determine a portion of the optical image corresponding to the region of interest; and
cause the portion of the anatomical image to be displayed over the portion of the optical image.

\* \* \* \* \*